US00PP34195P2

(12) United States Plant Patent
Shipley

(10) Patent No.: US PP34,195 P2
(45) Date of Patent: May 3, 2022

(54) ***HESPERALOE PARVIFLORA* PLANT NAMED 'STOP LIGHTS'**

(50) Latin Name: *Hesperaloe parviflora*
Varietal Denomination: Stop Lights

(71) Applicant: Nicholas Benoit Shipley, Tucson, AZ (US)

(72) Inventor: Nicholas Benoit Shipley, Tucson, AZ (US)

( * ) Notice: Subject to any disclaimer, the term of this patent is extended or adjusted under 35 U.S.C. 154(b) by 0 days.

(21) Appl. No.: 17/300,551

(22) Filed: Aug. 16, 2021

(51) Int. Cl.
*A01H 5/02* (2018.01)
*A01H 6/12* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt

(57) ABSTRACT

A new and distinct *Hesperaloe parviflora* named 'Stop Lights' is characterized by a plant size smaller and with lower growth vigor than is typical for *Hesperaloe parviflora*, brighter, more broadly opening red flowers than is typical for the species, a long bloom period without the production of fruits or seeds, producing bulbils on the spent inflorescences.

3 Drawing Sheets

Latin name: *Hesperaloe parviflora.*
Varietal denomination: 'Stop Lights'.

BACKGROUND OF THE INVENTION

The present invention relates to a new and distinct cultivar of *Hesperaloe parviflora*. The cultivar originated from a seed growout from a proprietary open pollinated breeding line of high diversity. The male plant was located within the same block of plants as the female parent since most pollination is by insects and no other *Hesperaloes* were close to the block from which seeds were collected. The breeding line is unnamed and since the seeds were collected from the entire breeding block and mixed it is not possible to determine which plant in the breeding line was either the specific female or male parent. One plant from this growout with unusual form and flower color for the species was selected and is the object of this application.

SUMMARY OF THE INVENTION

Among the features that distinguish the new *Hesperaloe parviflora* cultivar from all other available and commercial varieties of *Hesperaloe parviflora* known to the inventor are the following combination of characteristics: plant size smaller and with lower growth vigor than is typical for *Hesperaloe parviflora*, bright red flowers which open much more broadly than is typical for the species, a long bloom period without the production of fruits or seeds, production of bulbils on the spent inflorescences.

*Hesperaloe parviflora* 'Stop Lights' has been successfully propagated from bulbils that form on spent inflorescences which are easily rooted without growth hormones, by division of the multiheaded plant crown at a nursery near Sahuarita, Ariz. and by tissue culture in an independent tissue culture lab.

The foregoing characteristics and distinctions come true to form and are established and transmitted through succeeding propagations. The present invention has not been evaluated under all possible environmental conditions, such that the phenotype may vary with variations in environment without a change in the genotype of the plant.

BRIEF DESCRIPTION OF THE DRAWINGS

The accompanying photographs illustrate *Hesperaloe parviflora* 'Stop Lights' growing near Sahuarita, Ariz., depicted in color as nearly correct as it is possible to make in a color illustration of the character.

DETAILED PLANT DESRIPTION

Figure 1:
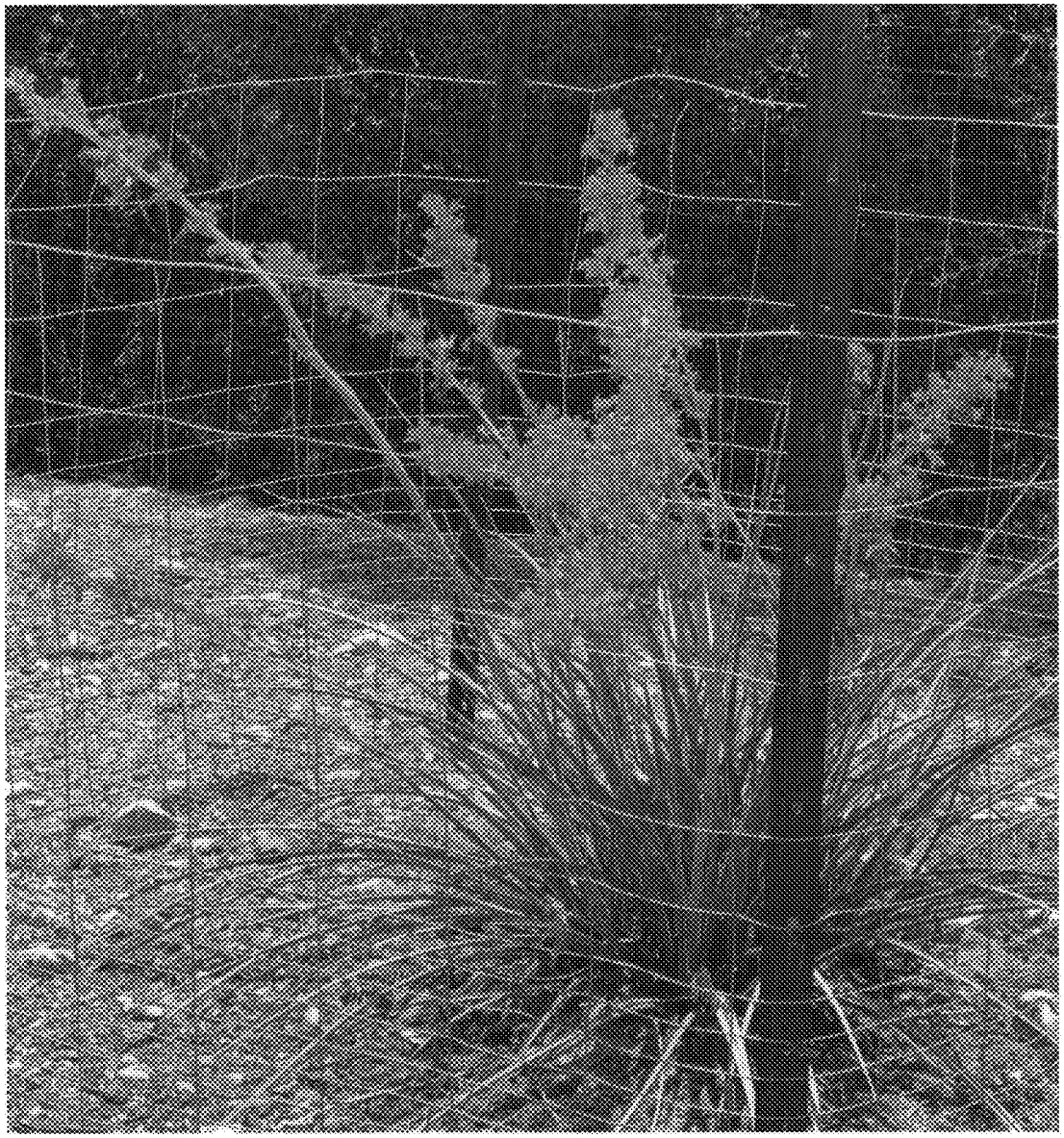
FIG. 1 shows *Hesperaloe parviflora* 'Stop Lights' growing in the ground in a nursery near Sahuarita, Ariz. aged 5 years.
Figure 2:
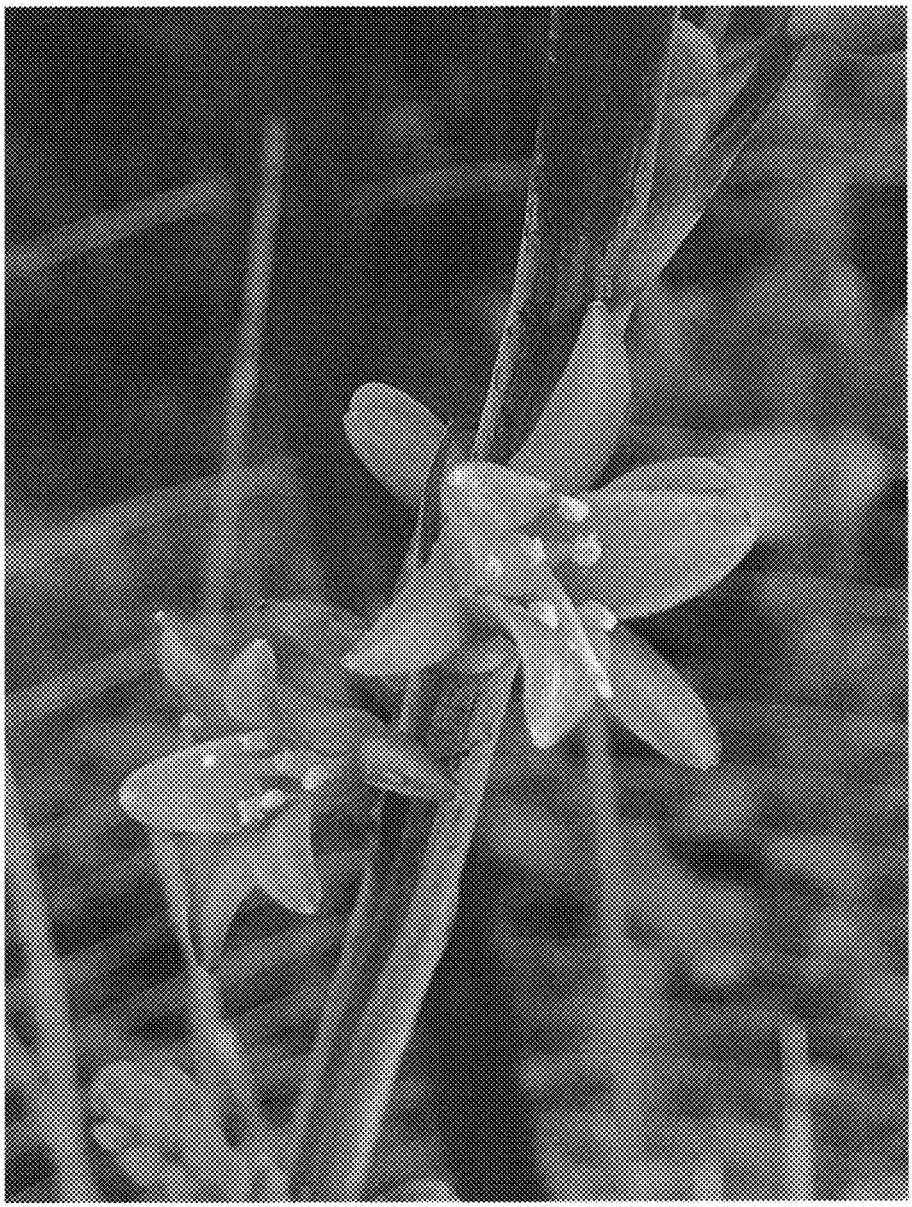
FIG. 2 shows a 'Stop Lights' flower at anthesis with dehisced and undehisced anthers with pollen present.
Figure 3:
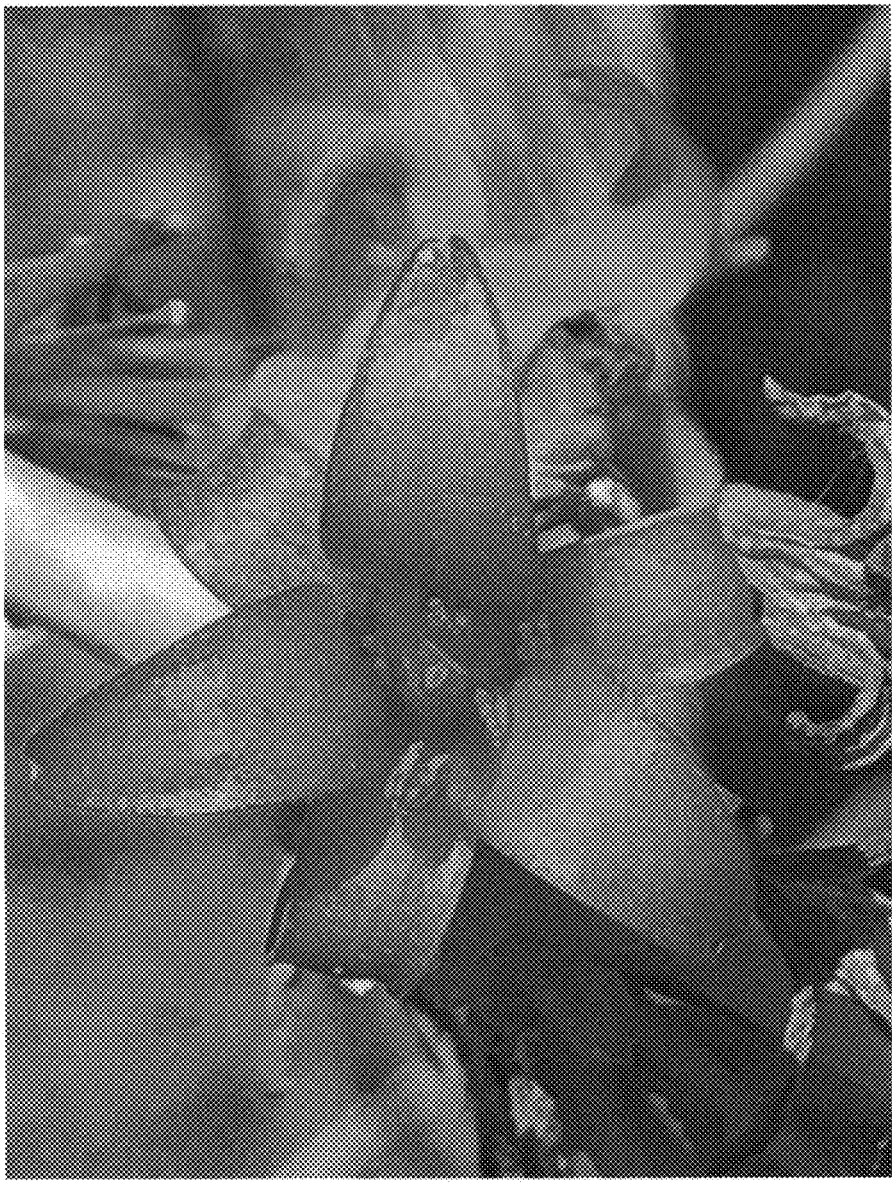
FIG. 3 shows a fully opened flower of 'Stop Lights' one day after anthesis with pollen removed by insects and anthers partially desiccated.

The following is a detailed description of the new *Hesperaloe parviflora* plant based upon the original 'Stop Lights' plant aged from 4 to 6 years of age (as noted below) growing in the ground with irrigation near Sahuarita, Ariz.

The color descriptions are based upon the 5th edition R.H.S. Colour Chart, copyright 2007. Color names other than common usage are as listed in *COLOR Universal Language and Dictionary of Names*, by Kenneth L. Kelly and Deane B. Judd; National Bureau of Standards special publication 440. Washington, D.C.: U.S. Department of Commerce, National Bureau of Standards, December 1976.

Plant is a clustering rosette semi-succulent long lived perennial with dark green, narrow, thickened leaves. Flowers are produced on arching spicate panicles which grow up to about 3 feet long. 'Stop Lights' is hardy to −20° F., USDA hardiness zone 5. No disease or insect problems were noted.

At age 6 years the plant measures about 1.5 feet tall and 3 feet across not counting the inflorescences. The plant consists of 14 individual rosettes connected to each other below ground level, each with from 5-15 leaves each.

Leaves vary in length from 11-55 cm in length. The described example was 55 cm long. At the midpoint of this leaf the leaf measured 5 mm wide×4 mm thick. The leaves are clasping at the base, fibrous internally, semisucculent and stiff. Leaves other than the basal portion of the leaf are linear, adaxially curled from the leaf edges, glabrous excluding the margins and the distal ⅓, finely striate the full length of the leaf (the striations more easily seen on the adaxial than the abaxial surface), with the surface scabrous on both sides of the distal ⅓ of the leaf, the leaf gradually tapers from the base to the apex, which is not sharp. The clasping portion of the leaf measures 17 mm wide×3 mm thick, color 157C. The color transitions gradually to 145B at 4 cm from the leaf base on the adaxial surface. The leaf measures 7 mm wide by 5 mm thick at this point. The color continues to change distally to an overall impression of color N138C for the majority of the adaxial surface. Microscopically this color breaks down to alternating bands about 0.12 mm wide of 138A with 188B.

On the abaxial surface the color changes rather abruptly about 1 cm from the leaf base from 157C to 143A. This color change continues to transition distally to an overall impression of color 139B for the majority of the abaxial surface. Under the microscope this color breaks down to alternating bands about 0.12 mm wide of 141C and 189C. The basal color 157C also extends gradually tapering out for about 2 cm inside the leaf margins of the abaxial side.

The basal leaf margin has a fragile, hyaline edge about 1 mm wide, color 162D, which is lined on the leaf side (axially) with N167A, also about 1 mm wide which runs from the leaf base to about 4 cm from the leaf base, where the hyaline edge gradually transitions into spiral fibers which extend forward and outward from the leaf and measure up to about 1 cm long. These fibers measure 0.12 mm in diameter with color NN155C. The brown (N167A) inner lining of the hyaline margin continues into the entirety of the length of the leaf margins with fibers, located just below the fibers on the leaf side. This lining narrows until it reaches the fiber bearing portion of the leaf. The line below the fibers is about 0.12 mm wide in the fibered portion of the leaf and is visible from both leaf surfaces and terminates along with the fibers at the ⅔ length point. The fibers are scattered along the leaf margins at irregular intervals starting from about 4 cm from the leaf base up to about ⅔ of the length of the leaf from the leaf base. The upper ⅓ of the leaf margin is microscopically denticulate.

Flowering of 'Stop Lights' occurs from May through October at the Sahuarita, Ariz. locality. Individual flowers last 3-4 days. The spent flowers fall away from the inflorescence about a week after anthesis. No floral aroma was noted.

The inflorescence is an apically blooming spicate panicle 3-3.5 feet long. Most flowering occurs on the upper ½ to ⅗ of the inflorescence. The inflorescence branches are spurs (shortened spikes) measuring 7-22 mm long and 4-6 mm wide excluding the persistent pedicel remnants, 12 mm wide including them. Each spur produces 5-20 flowers. The spurs alternate along the main axis of the inflorescence. These spurs are subtended by leaflike bracts which diminish in size from the lower flowering spurs toward the upper spurs. The lower spur bracts measure 12 cm long by 5 cm wide (near the bract base) and are linear, tapering apically. The upper spur bracts measure 4 cm long by 10 mm wide and are linear and apically tapering. The intermediate bracts grade in size between the lower ones and the upper ones. The main body of the spur bracts is glaucous and colored 146D. The spur bracts have a colored margin 1-2 mm wide at the base tapering to less than 0.5 mm wide near the bract apex. The margins are entire and colored 200B. The spur bracts are curled adaxially along their length, but less strongly so than the true leaves of the plant.

The peduncle is terete, basally measuring 9 mm in diameter, tapering to 2 mm in diameter at the apical spurs. The peduncle surface is smooth, glabrous and glaucous (especially the lower peduncle). Color is 193A at the peduncle base gradually transitioning to 146D in the upper portions of the inflorescence. Young, actively growing portions of the inflorescence axis within the flowering portion are colored N57A and as the axis matures it gradually changes color to 186C and finally at full maturity to 146D.

The mature buds of *Hesperaloe parviflora* 'Stop Lights' are ovoid in shape, measuring from 16-18 mm in length and 7.5-8 mm in diameter. The bud surface is glabrous and slightly glaucous, colored 51A from the base to about the midpoint, then grading to 58A at the apex. Pedicels are terete, measuring 8-12 mm in length×1 mm in diameter, color 46A. Flowers are actinomorphic, very nectiferous, with 3 glabrous sepals and 3 glabrous petals (both fused with the receptacle), which are similar in appearance and color, except the sepals are slightly narrower than the petals. The fully opened flowers are flaring, measuring 20 mm in diameter. The receptacle (color 51A) is discoid in shape with a conical base. The base measures 2 mm in diameter at the flared (receptacle) end and 1 mm in diameter at the base attachment to the pedicel, where there is an abscission layer. The discoid portion of the receptacle (color 51A) measures 5 mm in diameter and 2 mm long. Sepals are lance ovate, measuring 16-17 mm long×4 mm wide, margin entire, apex rounded acute, color N57A. Petals are lance ovate, 16-17 mm long×5 mm wide, margin entire, apex rounded acute, color N57A. Six stamens are attached to the receptacle, each one centered along the axis of a sepal or petal. The stamens are 12-14 mm in length, terete in cross section. The filaments measure 9-10 mm long, strongly tapering from the base to the anthers, basally 1.5 mm in diameter, apically 0.5 mm in diameter. The color of the filament grades from 63C at the base to N155C at the anther base. The filaments are glabrous. Anthers are dorsifixed near the base, nearly erect but slightly curved to the attachment side. Anthers are tardily dehiscent. Anthers measure 3 mm long×1.5 mm diameter, color 4C. Pollen is 100μ long×30μ wide, color 4C. The Pistil measures 14-18 mm long. The ovary, containing 3 carpels, color 4C, is ovoid in overall shape and somewhat angled at the middle of the carpels. The style measures 9-11 mm long and is laterally flattened, measuring 1 mm×2 mm in diameters at the base (color 155D) and tapering to 0.5 mm×0.3 mm at the stigma (color 65B). The color change in the style is gradually transitional from the base to the stigma. The stigma is relatively flat and oblique to the axis of the pistil, color N155D. The stigma is about 0.5 mm long×0.3 mm wide.

Fruits and seeds were not observed for the six years the original plant has been growing. Either the plants are infertile or self incompatible. After flowering is completed on a flowering stalk, one to several bulbils frequently appear at the base of an old flowering spur. The bulbils look like small, juvenile forms of the mother plant with 3-5 leaves each, the leaves having entire margins with a band of color N167A 1 mm wide along the margin. The bulbil base is colored N57A. This color transitions to the normal leaf color within the first 1-2 cm above the bulbil base. Leaves on the bulbils measure 2-12 cm in length×3-6 mm in width. The leaves are strongly curled from the margins to the axis on the adaxial side and erect to mildly outcurved lengthwise away from the bulbil axis. The bulbil leaves are glaucous and the main color other than previously described is 138C on both the adaxial and abaxial surfaces. The striations seen in normal, mature leaves are less noticeable on bulbil leaves.

COMPARISONS TO RELATED *HESPERALOES*

Compared to its parents, referring to the general characteristics typically seen in the parental breeding line as opposed to specific individual plants, *Hesperaloe parviflora* 'Stop Lights' is a smaller, less vigorous plant with redder flowers that open more broadly than is generally seen in the parental line. Additionally, the parental line produces at least some fruits and seeds, while 'Stop Lights' has produced no fruit over a period of 6 years.

Compared to *Hesperaloe parviflora* 'Yellow' (unpatented), 'Stop Lights' may be distinguished by the different flower color. 'Yellow' has yellow flowers while 'Stop Lights' flowers are bright red. Additionally the 'Stop Lights' plant is smaller with darker green leaves than 'Yellow'.

Compared to *Hesperaloe parviflora* 'Desert Flamenco' (not patented), 'Stop Lights' has red flowers while those of 'Desert Flamenco' are bicolored pink/light orange. Also 'Desert Flamenco' has a more highly branched inflorescence than 'Stop Lights. The plant of 'Desert Flamenco' is larger than that of 'Stop Lights'.

*Hesperaloe campanulata* 'MSWNNuevo Leon' (U.S. Plant Pat. No. 32,069) is compared since *Hesperaloe campanulata* and *parviflora* are similar and related species. The two cultivars are quite easily separated as 'MSWNNuevo Leon' is a much larger plant with inflorescences much more branched and three times the size of 'Stop Lights'. Also 'MSWNNuevo Leon' has pink flowers compared to red flowers on 'Stop Lights'.

*Hesperaloe parviflora* 'MSWNPerma' (U.S. Plant Pat. No. 28,909) may be distinguished from 'Stop Lights' by flower colors. 'MSWNPerma' flowers are bicolored pink/yellow compared to bright red on 'Stop Lights'. 'MSWNPerma' also has branched inflorescences while those of 'Stop Lights' are spicate. Leaves are considerably larger on 'MSWNPerma'.

*Hesperaloe parviflora* 'Perpa' (U.S. Plant Pat. No. 21,729) has smaller flowers with a different color than 'Stop Lights'. 'Stop Lights' flowers are colored N57A while those of 'Perpa' are listed as 53D at full flower opening. 'Perpa' plants are about ⅔ the size of 'Stop Lights' plants. 'Perpa' produces fruits and seeds, while 'Stop Lights' is seedless.

*Hesperaloe parviflora* X *funifera* 'Night Lights' (not patented) is a much larger plant than 'Stop Lights' with white, rather than red flowers.

*Hesperaloe funifera* X *parviflora* 'Perfu' (U.S. Plant Pat. No. 21,728) has inflorescences 8 feet tall with pink flowers arising from a 4 foot wide plant, while 'Stop Lights' inflorescences are 3-3.5 feet tall with bright red flowers and plants 3 feet wide.

*Hesperaloe parviflora* 'Coral Glow' (U.S. Plant Pat. No. 29,626) has bicolored peach/yellow flowers compared to the bright red flowers of 'Stop Lights'. Also, the flowers of 'Stop Lights' open much wider than 'Coral Glow'. 'Coral Glow' has a substantially taller inflorescence than 'Stop Lights'.

*Hesperaloe parviflora* 'MSWNPered' (U.S. Plant Pat. No. 28,910) may be distinguished from 'Stop Lights' by its campanulate flowers which open less broadly than 'Stop Lights', as well as the different flower color (N57A for 'Stop Lights, 53C-D for 'MSWNPered'). The inflorescence of 'MSWNPered' is also has more secondary branching than is seen in 'Stop Lights'.

*Hesperaloe parviflora* X *funifera* 'Night Lights' (not patented) is a much larger plant than 'Stop Lights' and has cream colored flowers compared to bright red on 'Stop Lights'.

I claim:

1. A new and distinct variety of *Hesperaloe parviflora* plant named 'Stop Lights' substantially as described and illustrated herein.

* * * * *